United States Patent [19]

Biesinger-Zwosta et al.

[11] Patent Number: 5,670,352
[45] Date of Patent: Sep. 23, 1997

[54] STABLE GROWTH TRANSFORMATION OF HUMAN T-LYMPHOCYTES BY *HERPESVIRUS SAIMIRI* (*H. SAIMIRI*) SUBGROUP C

[75] Inventors: Brigitte Biesinger-Zwosta, Uttenreuth; Ingrid Mueller-Fleckenstein; Bernhard W. Fleckenstein, both of Wiesenthau, all of Germany

[73] Assignee: Behringwerke Aktiengesellschaft, Marburg, Germany

[21] Appl. No.: 428,477

[22] Filed: Apr. 27, 1995

Related U.S. Application Data

[63] Continuation of Ser. No. 178,366, Jan. 6, 1994, abandoned, which is a continuation of Ser. No. 33,781, Mar. 18, 1993, abandoned.

[51] Int. Cl.$^6$ .............................. C12N 5/10; C12N 15/63; C12N 15/64
[52] U.S. Cl. ............................... 435/172.3; 435/240.2; 435/320.1
[58] Field of Search ................... 435/69.1, 172.1, 435/172.3, 240.2, 240.21, 320.1; 424/93.1, 93.2, 93.21

[56] References Cited

U.S. PATENT DOCUMENTS 4,690,915  9/1987  Rosenberg ........................ 514/2

OTHER PUBLICATIONS

"Report and Recommendations of the Panel to Assess the NiH Investment in Research on Gene Therapy", S.H. Orkin and A.G. Motulsky, Co–chairs, Dec. 7, 1995.
Biesinger, B. et al. 1992 Proc. Natl. Acad. Sci. USA vol 89 pp. 3116–3119.
Mittrucker, H.W. et al. 1992 J. Exp. med. vol 176 pp. 905–913.
Grassman, R. et al. 1989, J. Virol. vol 63 pp. 1818–1821.
Fleckenstein, B. et al., "*Herpesvirus saimiri* and *Herpes virus ateles*", in The Herpesviruses, vol. 1, pp. 253–331 (B. Roizman ed. 1982).
Schirm, S. et al., J. Virol., "Herpesvirus saimiri DNA in a Lymphoid Cell Line Established by In Vitro Transformation", 49:938–946 (Mar. 1984).
Desrosiers, R.C. et al., J. Virol., "Nononcogenic Deletion Mutants of Herpesvirus Saimiri Are Defective for In Vitro Immortalization", 57:701–705 (Feb. 1986).
Desrosiers, R.C. et al., Science, "A Region of the Herpesvirus saimiri Genome Required for Oncogenicity", 228:184–187 (Apr. 1985).
Desrosiers, R.C. et al., J. Virol., "Herpesvirus saimari Strain Variability", 43:352–356 (Jul. 1982).
Medveczky, P. et al., J. Virol., "Classification of Herpesvirus Saimiri Into Three Groups Based on Extreme Variation in a DNA Region Required for Oncogenicity", 52:938–944 (Dec. 1984).
Medveczky, M. et al., J. Virol., "Herpesvirus Saimiri Strains from Three DNA Subgroups Have Different Oncogenic Potentials in New Zealand White Rabbits", 63:3601–3611 (Sep. 1989).

Simmer, B. et al., J. Gen. Virol. "Persistance of selectable herpesvirus saimiri in various human haematopoietic and epithelial cell lines", 72:1953–1958 (1991).
Kaschka–Dierich, C. et al., J. Virol., "Structure of Nonintegrated, Circular Herpesvirus saimiri and Herpesvirus ateles Genomes in Tumor Cell Lines and In Vitro–Transformed Cells", 44:295–310 (Oct. 1982).
Grassman, R. et al., J. Virol., "Selectable Recombinant Herpesvirus Saimiri Is Capable of Persisting in a Human T–Cell Line", 63:1818–1821 (Apr. 1989).
Alt, M. et al., Gene, "A pair of selectable herpesvirus vectors for simultaneous gene expression in human lymphoid cells", 102:265–269 (1991).
Gardella, T. et al., J. Virol., "Detection of Circular and Linear Herpesvirus DNA Molecules in Mammalian Cells by Gel Electrophoresis", 50:248–254 (1984).
Valerius, T. et al., J. Immunol., "Effects Of IFN On Human Eosinophils In Comparison With Other Cytokines", 145:2950–2958 (Nov. 1990).
Kiyotaki, M. et al., J. Exp. Med., "Herpesvirus Saimiri Strain 11 Immortalizes A Restricted Marmoset T8 Lymphocyte Subpopulation In Vitro", 164:926–931 (Sep. 1986).
Bornkamm, G. et al., J. Virol., "Structure of Herpesvirus saimiri Genomes: Arrangement of Heavy and Light Sequences in the M Genome", 19:154–161 (Jul. 1976).
Albrecht, J. et al., Virology, "Structural Organization of the Conserved Gene Block of Herpesvirus saimiri Coding for DNA Polymerase, Glycoprotein B, and Major DNA Binding Protein", 174:533–542 (1990).
Bankier, A.T. et al., J. Virol., "Terminal Repetitive Sequences in Herpesvirus Saimiri Virion DNA", 55:133–139 (Jul. 1985).
Biesinger, B. et al., Virology, "The Divergence between Two Oncogenic Herpesvirus saimiri Strains in a Genomic Region Related to the Transforming Phenotype", 176:505–514 (1990).
Lee, S.I. et al., Cell, "Four Novel U RNAs Are Encoded by a Herpesvirus", 54:599–607 (1988).
Trimble, J.J. et al., Science, "A Gene for Dihydrofolate Reductase in a Herpesvirus", 239:1145–1147 (Mar. 1988).
Biesinger, B. et al., Proc. Natl. Sci. Acad. Sci. USA, "Stable Growth Transformation of Human T Lymphocytes by Herpesvirus Saimiri", 89:3116–3119 (Apr. 1992).
Mittrucker, H. et al., J. Exp. Med., "CD2–mediated Autocrine Growth of Herpes Virus Saimiri–transformed Human T Lymphocytes", 176:909–913 (Sep. 1992).

*Primary Examiner*—David Guzo
*Attorney, Agent, or Firm*—Finnegan, Henderson, Farabow, Garrett & Dunner, L.L.P.

[57] ABSTRACT

The invention concerns the transformation of human T-lymphocytes to stable growth by infecting said T-cells with strains of *H. saimiri* subgroup NonA NonB, preferably subgroup C. The transformed cells grow independently of antigen stimulation and can have a phenotype of activated mature T-lymphocytes, expressing cell surface markers characteristic for the distinct differentiation status of the T-cells. Infection with strains of *H. saimiri* belonging to the subgroups above can thus be used to generate human T-cell lines for a variety of immunological and biochemical applications as well as for therapeutic use.

23 Claims, 1 Drawing Sheet

STABLE GROWTH TRANSFORMATION OF HUMAN T-LYMPHOCYTES BY *HERPESVIRUS SAIMIRI* (*H. SAIMIRI*) SUBGROUP C

This application is a continuation of application Ser. No. 08/178,366, filed Jan. 6, 1994, now abandoned, which is a continuation of application Ser. No. 08/033,781, filed Mar. 18, 1993, now abandoned.

The invention concerns the transformation of human T-lymphocytes to stable growth by infecting said T-cells with strains of *H. saimiri* subgroup NonA NonB, preferably subgroup C. The transformed cells grow independently of antigen stimulation and can have a phenotype of activated mature T-lymphocytes, expressing cell surface markers characteristic for the distinct differentiation status of the T-cells. Infection with strains of *H. saimiri* belonging to the subgroups above can thus be used to generate human T-cell lines for a variety of immunological and biochemical applications as well as for therapeutic use.

Studies of normal human lymphocyte function are largely dependent on clones of stimulated cells since tumor lines usually express aberrant phenotypes and have modified functional properties. Expansion of human B-lymphocyte cultures by infection with the Epstein-Barr virus, a gamma$_1$ herpesvirus, has provided continuously growing human B cells for the study of B-cell differentiation and immunoglobulin synthesis. The distantly related gamma$_2$ prototype, *H. saimiri*, is indigenous to and apathogenic in squirrel monkeys (Fleckenstein, B. & Desrosiers, R. C. (1982) in The Herpesviruses, ed. Roizman, B. (Plenum, New York), Vol. 1, pp. 253–331) but causes fulminant T-cell lymphomas and acute lymphocytic leukemias in other New World primates (Fleckenstein, B. & Desrosiers, R. C. (1982) loc. cit.) and rabbits.

It also immortalizes cultured peripheral blood lymphocytes of cotton top marmosets (*Saguinus oedipus*) (Schirm, S. et al. (1984) J. Virol. 49, 938–946) and common marmosets (*Callithrix jacchus*) (Desrosiers, R. C. et al. (1986) J. Virol. 57, 701–705). Genes required for lymphocyte growth transformation and oncogenicity were localized to the left terminal region of the 112-kilobase-pair (kbp) L-DNA in the *H. saimiri* genome (Desrosiers, R. C. et al. (1985) Science 228, 184–187). Based on extreme sequence variations at the same left terminus of L-DNA, the known *H. saimiri* strains have been divided into subgroups (A, B, and C as well as NonA NonB) (Desrosiers, R. C. & Falk, L. A. (1982) J. Virol. 43, 352–356; Medveczky, P. et al. (1984) J. Virol. 52, 938–944) that differ in their oncogenic capacity (Medveczky et al. (1989) J. Virol. 63, 3601–3611).

Convenient protocols for the immortalization of human T-cells by viruses have been lacking up to now. Expansion of primary T-lymphocytes by repeated antigen or phytohemagglutinin (PHA) stimulation and cloning of these cells is laborious and usually yields limited numbers of cells growing <1 year. Immortalization with human T-cell leukemia virus type I (HTLV-I) is limited in terms of frequency and by its CD4 specificity. *H. saimiri* is able to transform monkey T-cells. Unlike Epstein-Barr virus or HTLV-I, penetration of *H. saimiri* into cells is not restricted by a membrane receptor limited to few cell types (Simmer, B. et al. (1991) J. Gen. Virol. 72, 1953–1958).

We have now elucidated that cultures of human mononuclear cells from peripheral blood, cord blood, or thymus infected with e.g. strains 484-77 and 488-77 of *H. saimiri* subgroup NonA NonB, preferably C yielded continuously growing lymphoblastoid cell lines, whereas all cells infected with strains 11 and OMI (group A) or SMHI (group B) and uninfected cells ceased to proliferate within approx. 4 weeks. The transformed cells can express the phenotype of mature activated T-cells, depending on medium conditions for proliferation.

In U.S. patent application Ser. No. 07/417,596 which is incorporated herein by reference the following is inter alia disclosed:

a) selectable *H. saimiri* recombinants which have a selection gene inserted in the right or left junction site or junction region of the H- and L-DNA, b) a process for the preparation of the recombinants specified under a) and c) the use thereof for the expression of foreign genes in human T-lymphocytes, as well as d) the generation of monkey T-cell lines which constitutively express a foreign gene by means of transformation-competent recombinant Herpesvirus saimiri.

"Foreign gene" in this context means any gene inserted into *H. saimiri* as disclosed above at a) including selection genes and as described in U.S. patent application Ser. No. 07/417,596, abandoned, in detail. Consequently the instant invention relates to a method of transforming human T-lymphocytes by infection with *H. saimiri* subgroup NonA NonB, preferably C and to the human T-lymphocytes transformed in this manner. Furthermore, the invention relates to expression of foreign genes in human T-lymphocytes which are thus transformed to stable growth. In some cases it is advantageous to insert alone or in addition a selection gene like e.g. the well-known neogene, thus making it possible to select for transformed, that is immortalized T-cells by adding e.g. geneticin.

Human T-cell lines which are transformed as disclosed supra are useful for a wide variety of applications. Efficient clonal expansion of differentiated human T-lymphocytes including CD8$^+$ cells is now possible by making use of the instant invention. Another application is permanent expansion of human CD4$^+$ or CD8$^+$ lines that are preselected by e.g. antigen stimulation, cell surface markers, function (e.g. cytotoxicity or helper function), secretion of distinct cytokine patterns. Treatments before immortalisation may include stimulation with a lectin such as phytohemagglutinin (PHA) or phorbol ester (PMA) or addition of regulatory factors such as immunomodulators comprising cytokines. However, it may be now possible to immortalize premature T-cells or T-cells without stimulation giving thus access to rare T-cell subpopulations not accessible up to now. In conjunction with expression of specific genes specifically inserted into the right or left junction site or junction region of the H- and L-DNA of *H. saimiri* the instant invention facilitates somatic gene therapy by e.g. curing genetic defects. This implies that uncontrolled proliferation of *H. Saimiri* transformed T-cells is prevented by established somatic gene therapy methods which allow "neutralization" of the *H. saimiri* transformative effect.

A still further application of the instant invention resides in the fact that valuable proteins e.g. regulatory factors or receptors for such factors produced by a particular human T-lymphocyte are now better accessible respective can now be isolated and purified by using the transformation method disclosed. In this case it can be advantageous to continue to treat the immortalized T-cells of the instant invention with stimulants exemplified above.

The instant invention facilitates likewise the screening for molecules that are produced by or interact with factors produced by human T-cells immortalized as above.

The immortalized human T-cells may also be used to induce tumors in in vivo systems such as in tolerant or immunosuppressed laboratory animals. By inoculating animals with transformed T-cells and possibly carrying suitable "foreign" genes in addition, it will be possible to induce a T-cell malignancy in those animals. These animals can be used in developing a method for screening compounds that are useful for treating the malignancy. For example one can use mice to establish a model system for treating human T-cell leukemias. One "infects" the laboratory animal with one of these transformed cell lines according to the invention. Thereafter, one would wait until a tumor developed and then add a predetermined compound to the animal, wait, and determine how the tumor and the animal responded. Alternatively, one could test for compounds that prevent the ocurrence of the disease by first adding a predetermined compound such as a vaccine, then inoculating the animal with a transformed cell line and waiting to see if the animal becomes "infected".

One can also use these immortalized cell lines in vitro to test various compounds on these cell lines and on control cell lines. This could be done by taking a sample containing an immortalized cell line and a sample containing another human cell line, adding predetermined substance to each and then determining the reaction of the two cell lines. This type of testing can be done serially or concurrently. Furthermore, various types of drugs can be tested for simply by changing the cell line used, for example using leukemia cells rather than T-cells or by introducing suitable "foreign genes" into the immortalized T-cells. Thus this system can be used to develop compounds that will treat human T-cell pathological conditions and especially leukemias.

Furthermore, the invention is detailed also in the patent claims and the examples. T-cell lines used here reflect a selection of available material and are by no means to be understood as being representative for all obtainable lines.

EXAMPLE 1

Infection of Human Mononuclear Cells with *H. saimiri* Subgroup A, B and C

Cultures of human mononuclear cells from peripheral blood, cord blood, or thymus infected with e.g. strains 484-77 and 488-77 of *H. saimiri* subgroup C (Desrosiers, R. C. et al., loc. cit.; Medveczky, P. et al., loc. cit.) yielded continuously growing lymphoblastoid cell lines, whereas all cells infected with strains 11 and OMI (group A) or SMHI (group B) and uninfected cells ceased to proliferate within approx. 4 weeks. Numerous lymphoid cell lines were consistently established by infection with the subgroup C strain 488, of which six lines were selected for further characterization (Table 1). All lines have been observed for at least 9 months. When total cellular DNA on Southern blots was hybridized with a 1.7-kbp AccI fragment from the left end of L-DNA, covering the transformation-associated gene (FIG. 1), genomic *H. saimiri* DNA sequences were found in all cell lines, except line PB-W, at 30–60 genome equivalents per diploid cellular genome. The lymphoid cell lines contained the multicopy viral genomes as episomes, as has been observed in lymphoma-derived monkey cells (Kaschka-Dierich, C. et al. (1982) J. Virol. 44, 295–310) and in persistently infected human tumor cell lines (Grassmann, R. & Fleckenstein, B. (1989) J. Virol. 63, 1818–1821; Alt, M. et al. (1991) Gene 102, 265–269). Estimates based on results of a polymerase chain reaction (PCR) indicated that the peripheral blood-derived line PB-W probably carries 1 genome copy per cell. The immortalized human lymphoblastoid lines did not secrete detectable amounts of infectious virus into the culture supernatant. Transcription of the putative oncogene STP-C488/ORF-2 (ORF=open reading frame) (Jung, J. U. et al., loc. cit.) was demonstrated in all cell lines by hybridization of RNA on Northern blots with ORF-2-specific primers (FIG. 1).

All cell lines tested expressed mature T-cell phenotypes ($CD2^+$, $CD3^+$, $CD5^+$, $CD7^+$, and $TCR1^+$) but did not have the markers CD1 and TCR2. All lines, except one (Lucas), were either $CD4^+CD8^-$ or $CD4^-CD8^+$ (Table 1). The thymus-derived cell line Lucas had a mixed phenotype.

Double-fluorescence analysis indicated that the Lucas cell line contains $CD4^+$ and $CD8^+$ single-positive cells and smaller subpopulations of CD4/8 double-positive and -negative cells. All cell lines were negative for the nonspecific NK cell marker CD57 (HNK-1). A second marker for lymphocytes with Natural Killer (NK) activity, CD56 (NKH-1), was found on all lines with the exception of PB-W. Strong cytotoxic activity on K562 cells was observed for the $CD8^+$ lines (Table 1). The $CD4^+CD8^-$ lines showed no (PB-W) or low (CB-15) NK activity. All cell lines appeared to represent activated T-cells expressing HLA-class II molecules and were positive for the T-cell activation marker CD30. They all expressed the interleukin 2 receptor β chain. No reactivity was observed with the pan-B-cell marker CD19.

EXAMPLE 2

Cell Culture and Infection

Peripheral blood leukocytes from healthy donors, cord blood leukocytes, or thymocytes from children undergoing cardiac surgery were used in two protocols. One procedure used centrifugation through Histopaque$^R$ density gradients (1.1 g/ml; Pharmacia) to isolate mononuclear cells, which were subsequently stimulated with phytohemagglutinin P (PHA, Sigma) for 1 day. Alternatively, erythrocytes were depleted from whole blood by dextran sedimentation, and leukocytes were sedimented from the supernatant. Thymocytes were extracted from minced thymus tissue. Stimulated and unstimulated cells were seeded into appropriate tissue culture plastic ware at a density of $1 \times 10^6$ cells per ml and inoculated with $10^4$–$10^6$ tissue culture infectious doses of virus. PHA-stimulated cells were supplemented with recombinant interleukin 2 (50 units/ml; Eurocetus, Amsterdam). Production of infectious virus was monitored by cocultivation of lymphocytes with permissive owl monkey kidney cells.

EXAMPLE 3

Detection of Viral DNA

Total cellular DNA was isolated and analyzed by Southern blot hybridization to the Acc I fragment specific for strains of group C (FIG. 1) according to standard protocols (Sambrook, J. et al. (1989) Molecular Cloning: A Laboratory Manual (Cold Spring Harbor Lab., Cold Spring Harbor, N.Y.). To determine whether the viral genome was integrated into cellular DNA or persisted as an episome, $1 \times 10^6$ cells were lysed on top of a 1% agarose gel by the procedure of Gardella et al. (Gardella, T., et al. (1984) J. Virol. 50, 248–254), and fractionated DNA was transferred to nitrocellulose filters. Hybridization was performed with a Kpn I fragment conserved in all virus strains (FIG. 1).

EXAMPLE 4

Analysis Surface Markers

Cells were incubated at $1$–$5 \times 10^5$ cells per well in 96-well microtiter plates. Monoclonal antibodies OKT4 (CD4, OKT6 (DC1), OKT8 (CD8), OKT11 (CD2), OKT26a (CD25), interleukin 2 receptor β chain), and OKB-PanB (CD19) (Ortho Diagnostics); Leu1 (CD5), Leu4 (CD3), Leu9 (CD7), and Leu19 (CD56, NKH-1) (Becton Dickinson); TCR1 [alpha/beta chains of T-cell receptor (TCR)], and TCR2 (gamma/delta chains of TCR) (T-Cell Sciences, Cambridge, Mass.); ATCC TIB200 (CD57, HNK-1), ATCC HB96 (HLA-class. II molecules), and Ki-1 (CD30) (Dianova, Hamburg, F.R.G.) were used for single-color flow microfluorometry (FMF). For double-color FMF Fluorescein isothiocyanate-conjugated anti-CD4 and phycoerythrin-labeled anti-CD8 antibodies (Immunotech, Marseille, France) were applied. After incubation for 30 min at 4° C., cells were washed and used for FMF double fluorescence or stained with fluorescein isothiocyanate-conjugated mouse anti-human IgG plus IgM (F(ab')$_2$ (Becton Dickinson) for single-color FMF. FMF analysis was performed using an electronically programmable individual cell sorter Epics Elite or Epics Profile, Coulter) (Valerius, T. et al. (1990) J. Immunol. 145, 2950–2958). Non-viable cells and cellular debris were gated out by propidium iodide staining and forward light scatter. NK activity was determined with a chromium release assay using K 562 cells (Kiyotaki, M. et al. (1986) J. Exp. Med. 164, 926–931).

BRIEF DESCRIPTION OF THE DRAWINGS

Legend to FIG. 1

Structural organization of the *H. saimiri* M-genome (Bornkamm, G. W. et al. (1976) J. Virol. 19, 154–161) and its left-terminal L-DNA. The 112-kbp L-DNA region encompasses four blocks of genes (arrows 1–4) that are partially conserved among all known herpesviruses (Albrecht, J. & Fleckenstein, B. (1990) Virology 174, 533–542); it is flanked by repetitive H-DNA (Bankier, A. T. et al. (1985) J. Virol. 55, 133–139). The left-terminal 6 kbp of L-DNA in strain 488-77 of group C are widely divergent from L-regions of virus strains of groups A and B (Biesinger, B. et al. (1990) Virology 176, 505–514). The region contains five U-RNA genes (solid arrows) (Biesinger, B. et al. loc. cit); Lee, S. I. et al. (1988) Cell 54, 599–607), a transcription unit for dihydrofolate reductase (DHFR) (Trimble, J. J. et al. (1988) Science 239, 1145–1147), and two open reading frames (ORF; ORF-1 and ORF-2/STP-C488) related to the oncogenic phenotype (Biesinger, B. et al., loc. cit.). The hybridization probe (Kpn I fragment) detecting nonintegrated viral DNA, the Acc I fragment used for Southern, and Northern blot analyes, and oligonucleotides for PCR amplification of viral DNA and mRNA are indicated.

Figure 1:
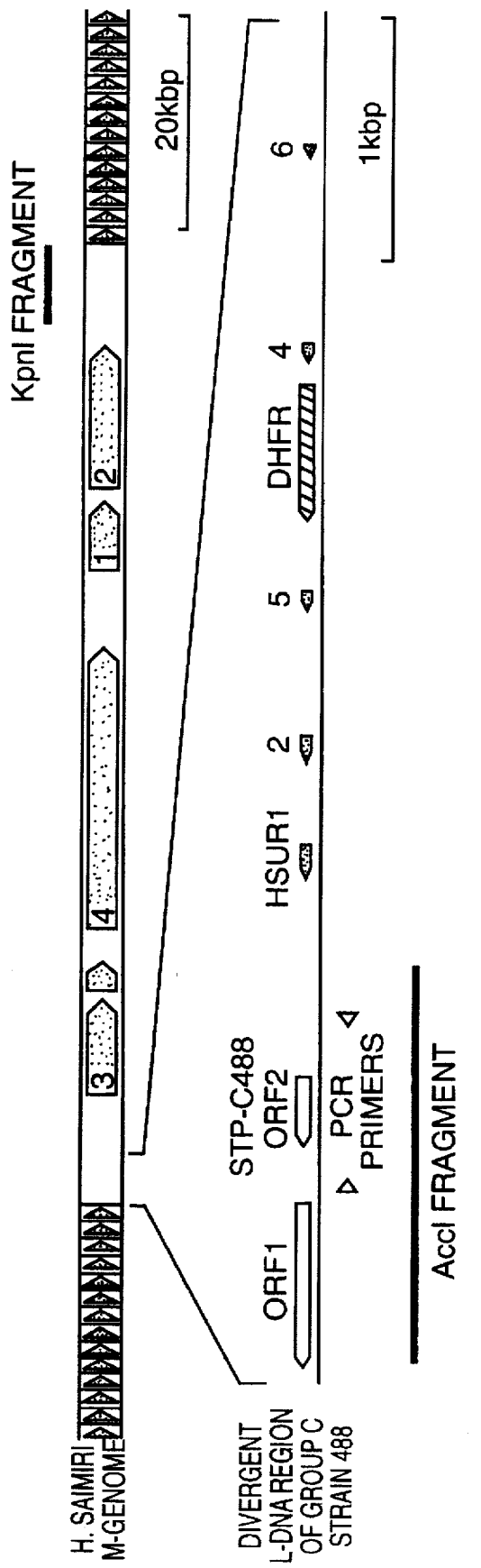

What is claimed is:

1. A method to immortalize a human T-lymphocyte cell, comprising the step of infecting said cell with *Herpesvirus saimiri* (*H. saimiri*) subgroup C virus.

2. The method according to claim 1, wherein in addition a foreign gene is inserted into *H. saimiri* subgroup C virus prior to infecting the human T-lymphocyte cell.

3. The method according to claim 1, wherein the human T-lymphocytes to be immortalized are preselected or pre-treated.

4. The method according to claim 1, wherein the human T-lymphocytes to be immortalized produce a valuable protein.

5. An immortalized cell line of human T-lymphocytes obtained by the process of claim 1.

6. The method according to claim 2, wherein said foreign gene is a selectable gene.

7. The method according to claim 2, wherein in addition to a first foreign gene inserted into the *H. saimiri* subgroup C virus a second foreign gene is inserted into the *H. saimiri* subgroup C virus.

8. The method according to claim 7, wherein the second foreign gene is a selectable gene.

9. The method according to claim 2, wherein the human T-lymphocytes to be immortalized are preselected or pre-treated.

10. An immortalized cell line of human T-lymphocytes obtained by the process of claim 2.

11. The method according to claim 6, wherein the human T-lymphocytes to be immortalized are preselected or pre-treated.

12. An immortalized cell line of human T-lymphocytes obtained by the process of claim 6.

13. The method according to claim 7, wherein additionally the transformative activity of *H. saimiri* is controlled.

14. An immortalized cell line of human T-lymphocytes obtained by the process of claim 7.

15. The method according to claim 8, wherein the selectable gene is the neo or hygromycin gene.

16. An immortalized cell line of human T-lymphocytes obtained by the process of claim 8.

17. An immortalized cell line of human T-lymphocytes obtained by the process of claim 15.

18. An immortalized cell line of human T-lymphocytes obtained by the process of claim 3.

19. An immortalized cell line of human T-lymphocytes obtained by the process of claim 9.

20. The method according to claim 11, wherein said valuable protein is a regulatory factor or a receptor for such regulatory factor.

TABLE 1

Origin and Surface properties of herpesvirus-transformed human cell lines

| Cell line | Origin | Donor sex/age | Stimulation of primary culture by PHA | Presence of surface marker | | | Cytotoxicity against K 562 cells |
|---|---|---|---|---|---|---|---|
| | | | | CD4 | CD8 | CD56 | |
| CB-15 | Cord blood | Newborn | − | + | − | + | + |
| P-1080 | Cord blood | Newborn | + | − | + | + | + |
| PB-W | Adult blood | Female/23 years | − | + | − | − | − |
| P-1083 | Adult blood | Female/26 years | + | − | + | + | + |
| Lucas | Thymus | Male/17 months | − | + | + | + | + |
| P-1084 | Thymus | Female/4.5 years | + | − | + | + | + |

All cells expressed CD2, CD3, CD5, CD7, CD25, CD30, TCR1, (alpha/beta chains), and HLA class II molecules and were negative for CD1, CD19, CD57, and TCR2 (gamma/delta)

21. An immortalized cell line of human T-lymphocytes obtained by the process of claim 11.

22. An immortalized cell line of human T-lymphocytes obtained by the process of claim 4.

23. An immortalized cell line of human T-lymphocytes obtained by the process of claim 20.

* * * * *